US010631803B2

(12) United States Patent
Ertel et al.

(10) Patent No.: US 10,631,803 B2
(45) Date of Patent: Apr. 28, 2020

(54) MEDICAL IMAGING SYSTEM FOR COMBINED MAGNETIC RESONANCE IMAGING AND X-RAY IMAGING

(71) Applicants: Dirk Ertel, Forchheim (DE); Yiannis Kyriakou, Spardorf (DE)

(72) Inventors: Dirk Ertel, Forchheim (DE); Yiannis Kyriakou, Spardorf (DE)

(73) Assignee: Siemens Healthcare GmbH, Erlangen (DE)

( * ) Notice: Subject to any disclaimer, the term of this patent is extended or adjusted under 35 U.S.C. 154(b) by 279 days.

(21) Appl. No.: 15/680,554

(22) Filed: Aug. 18, 2017

(65) Prior Publication Data
US 2018/0049708 A1 Feb. 22, 2018

(30) Foreign Application Priority Data

Aug. 18, 2016 (DE) .................. 10 2016 215 460

(51) Int. Cl.
A61B 6/00 (2006.01)
A61B 5/055 (2006.01)
(Continued)

(52) U.S. Cl.
CPC ............ *A61B 6/4411* (2013.01); *A61B 5/055* (2013.01); *A61B 6/4417* (2013.01);
(Continued)

(58) Field of Classification Search
CPC ... A61B 6/4411; A61B 6/4417; A61B 6/4429; A61B 5/055; G01R 33/4812; G01N 23/044
See application file for complete search history.

(56) References Cited

U.S. PATENT DOCUMENTS 10,390,777 B2 * 8/2019 Risher-Kelly ......... A61B 6/032
2004/0022350 A1 * 2/2004 Gregerson ............ A61B 6/032
378/15

(Continued)

FOREIGN PATENT DOCUMENTS

DE 102006042572 A1 3/2008
DE 102008034578 A1 2/2010
WO WO2014044314 A1 3/2014

OTHER PUBLICATIONS

German Office Action for related German Application No. 10 2016 215 460.5 dated Apr. 25, 2017.

*Primary Examiner* — Carolyn A Pehlke
(74) *Attorney, Agent, or Firm* — Lempia Summerfield Katz LLC

(57) ABSTRACT

For the purpose of reliable and comprehensive patient care, a medical imaging system for combined magnetic resonance and X-ray imaging is provided. The medical imaging system includes a magnetic resonance imaging unit and an X-ray imaging unit that are connected to each other mechanically such that the X-ray imaging unit is built into the magnetic resonance imaging unit and both units surround a patient aperture. The X-ray imaging unit includes a ring that has an X-ray tube and an X-ray detector and may rotate about the patient aperture. The ring is composed of at least four ring sectors, of which two ring sectors may be detached from the ring and at least two ring sectors are fixed in place. An X-ray detector is arranged on one of the detachable ring sectors, and an X-ray source is arranged on the other of the detachable ring sectors.

15 Claims, 5 Drawing Sheets

(51) Int. Cl.
*G01N 23/046* (2018.01)
*G01R 33/48* (2006.01)

(52) U.S. Cl.
CPC ......... *A61B 6/4429* (2013.01); *G01N 23/046* (2013.01); *G01R 33/4812* (2013.01)

(56) References Cited

U.S. PATENT DOCUMENTS

| | | | |
|---|---|---|---|
| 2008/0061241 A1 | 3/2008 | Rietzel | |
| 2010/0033186 A1 | 2/2010 | Overweg et al. | |
| 2011/0280364 A1* | 11/2011 | Maschke | A61B 6/037 378/4 |
| 2015/0230766 A1* | 8/2015 | Wang | A61B 6/032 600/411 |
| 2015/0247907 A1 | 9/2015 | Heid | |
| 2016/0015344 A1* | 1/2016 | Fortuna | A61B 6/4435 378/51 |
| 2018/0325477 A1* | 11/2018 | Wang | A61B 5/055 |

\* cited by examiner

MEDICAL IMAGING SYSTEM FOR COMBINED MAGNETIC RESONANCE IMAGING AND X-RAY IMAGING

This application claims the benefit of DE 10 2016 215 460.5, filed on Aug. 18, 2016, which is hereby incorporated by reference in its entirety.

BACKGROUND

The present embodiments relate to a medical imaging system for combined magnetic resonance and X-ray imaging.

Magnetic resonance imaging is a proven patient examination method in medical imaging. A major advantage of magnetic resonance imaging is the excellent soft-tissue contrast in the representation of the subject under examination. Magnetic resonance imaging still has limitations, some of which are inherent while some are also due to conditions specific to acquiring a magnetic resonance image (MRI) dataset. These limitations are at the expense of the image quality of the MRI dataset. For example, a large amount of time may be needed for acquisitions at high spatial resolution, which provides that movements in the acquisition region may cause interference. Approaches to reducing the measurement periods for MRI datasets include, for example, subsampling the k-space, which may result in limitations to the image quality. Another challenge is the homogeneity of the magnetic resonance fields used, where even small variations in the homogeneity may manifest clearly in limitations to the image quality.

Medical imaging systems configured to compensate for these limitations that constitute a combination of a magnetic resonance imaging unit and another imaging modality (e.g., an X-ray imaging unit) are known. For example, medical imaging systems for combined magnetic resonance and X-ray imaging, in which an X-ray imaging unit including an X-ray source and an X-ray detector has been fully integrated mechanically into a magnetic resonance imaging unit, have been proposed. It is hence possible to acquire MRI datasets and X-ray imaging datasets simultaneously. The X-ray tube/detector system is typically mounted on a closed ring for this purpose. This ring is embedded in the MR gantry (e.g., located in the center of the MR gantry, between the gradient coils). This complete mechanical integration of the X-ray tube/detector system entails additional challenges, however. The access required to specific technical components (e.g., X-ray tube) is severely restricted. Necessary servicing or assembly work or simply replacing faulty components (e.g., replacing a faulty X-ray tube) is not possible. Moreover, there are not meant to be any restrictions on the use of the angio-MR system for medical applications.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a medical imaging system for combined magnetic resonance and X-ray imaging that reduces the disadvantages of the prior art is provided.

A medical imaging system for combined magnetic resonance and X-ray imaging includes a magnetic resonance imaging unit and an X-ray imaging unit that are connected to each other mechanically such that the X-ray imaging unit is built into the magnetic resonance imaging unit and both units surround a patient aperture.

The medical imaging system according to an embodiment for combined magnetic resonance and X-ray imaging is configured such that the X-ray imaging unit includes a ring that has an X-ray tube and an X-ray detector and may rotate about the patient aperture, such that the ring is composed of at least four ring sectors. Two ring sectors of the at least four ring sectors may be detached from the ring. The medical imaging system is configured such that at least two ring sectors are fixed in place. An X-ray detector is arranged on one of the detachable ring sectors, and an X-ray source is arranged on the other of detachable ring sectors.

The X-ray imaging unit inside the medical imaging system for combined magnetic resonance and X-ray imaging allows easy access with little effort to specific technical components of the X-ray tube/detector system, while allowing high functionality of the system. The use of at least four ring sectors and the detachability of the ring sectors on which the X-ray source and the X-ray detector are arranged makes it possible to perform necessary servicing work, assembly tasks, and replacement of faulty components quickly without interfering with clinical operation in the long-term. Arranging the X-ray imaging unit inside the magnetic resonance imaging unit provides that both MRI datasets and X-ray imaging datasets of the same subject under examination may be acquired quickly and without interference.

The magnetic resonance imaging unit may include a solenoid that surrounds the X-ray imaging unit.

According to one embodiment, the detachable ring sectors are formed such that the detachable ring sectors may be detached from the ring towards the patient aperture. This minimizes the effort involved in removing the relevant components, because the patient aperture is generally empty when an examination is not in progress, and hence, the components may be taken out quickly and easily.

For quick removal, the detachable ring sectors are advantageously connected to the fixed ring sectors using releasable connecting elements. The releasable connecting elements may include screws and/or pins and/or guide sleeves and/or hinged fasteners, for example.

According to another embodiment, at the points of connection to the fixed ring sectors, the detachable ring sectors include guide elements having complementary guide profiles. By virtue of these complementary guide profiles, the ring sectors may be connected to one another easily and without errors. Only the matching ring sector may be inserted. The guide profiles facilitate easy detachability by sliding in the relevant direction.

For reliable X-ray imaging, the ring includes an electric drive having at least two drive elements and a plurality of ring-gear elements that engage with one another and cause the ring to rotate.

According to another embodiment, the imaging system includes a lifting system for automatic removal of the ring sectors from the system.

The lifting system is configured to be able to dock onto the detachable ring sectors.

DETAILED DESCRIPTION

Figure 1:
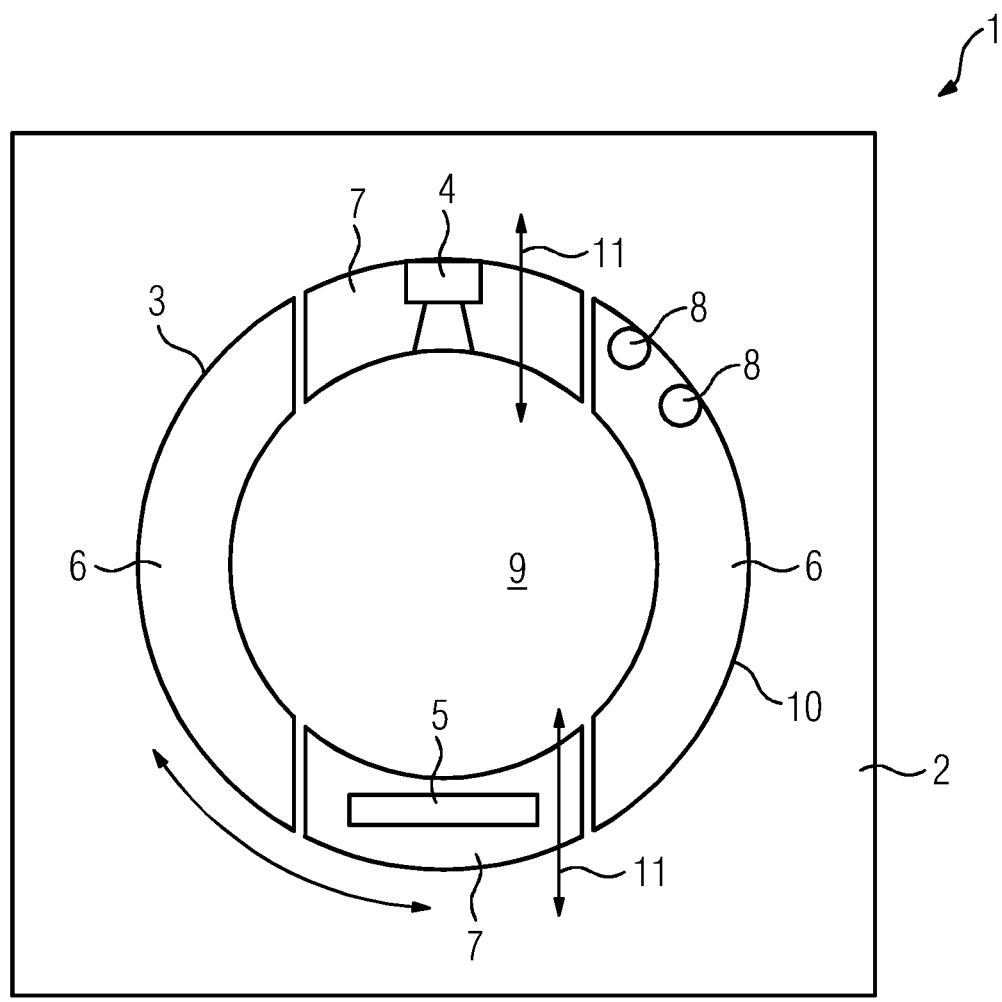
FIG. 1 shows a view of a medical imaging system according to an embodiment for combined magnetic resonance and X-ray imaging.

FIG. 1 shows one embodiment of a medical imaging system 1 for combined magnetic resonance and X-ray imaging including a magnetic resonance imaging unit 2 and an X-ray imaging unit 3. Such combined imaging systems are generally known, for example, from WO 2014/044314 A1. In this system, the X-ray imaging unit 3 is built into the magnetic resonance imaging unit 2 and both units surround a patient aperture 9, in which a patient is supported during an examination. The magnetic resonance imaging unit 2 (e.g., including a gantry) may include a solenoid or permanent magnets, for example, that surrounds the X-ray imaging unit 3.

The X-ray imaging unit 3 includes a ring 10 that includes at least four ring sectors 6, 7. The ring 10 is configured such that the ring 10 may rotate about a center of rotation located in the region of the patient aperture. The ring 10 also includes an X-ray tube 4 and an X-ray detector 5 that lie on opposite sides from each other with respect to the center of rotation. These components may be used to allow rotation about the patient aperture and LAO/RAO angulation for X-ray imaging. The four ring sectors 6, 7 are configured such that two fixed ring sectors 6 are permanently attached and two detachable ring sectors 7 may be detached from the ring 10 and removed. The detachable ring sectors 7 may be moved towards the patient aperture and removed, which is shown in FIG. 1 by the movement arrow 11.

In addition, the ring 10 has releasable connections between the detachable ring sectors 7 and the fixed ring sectors 6. The detachable ring sectors 7, to which the X-ray tube 4 and the X-ray detector 5 are attached, may thereby be detached from the closed ring and taken out of the gantry of the medical imaging system 1.

Figure 2:
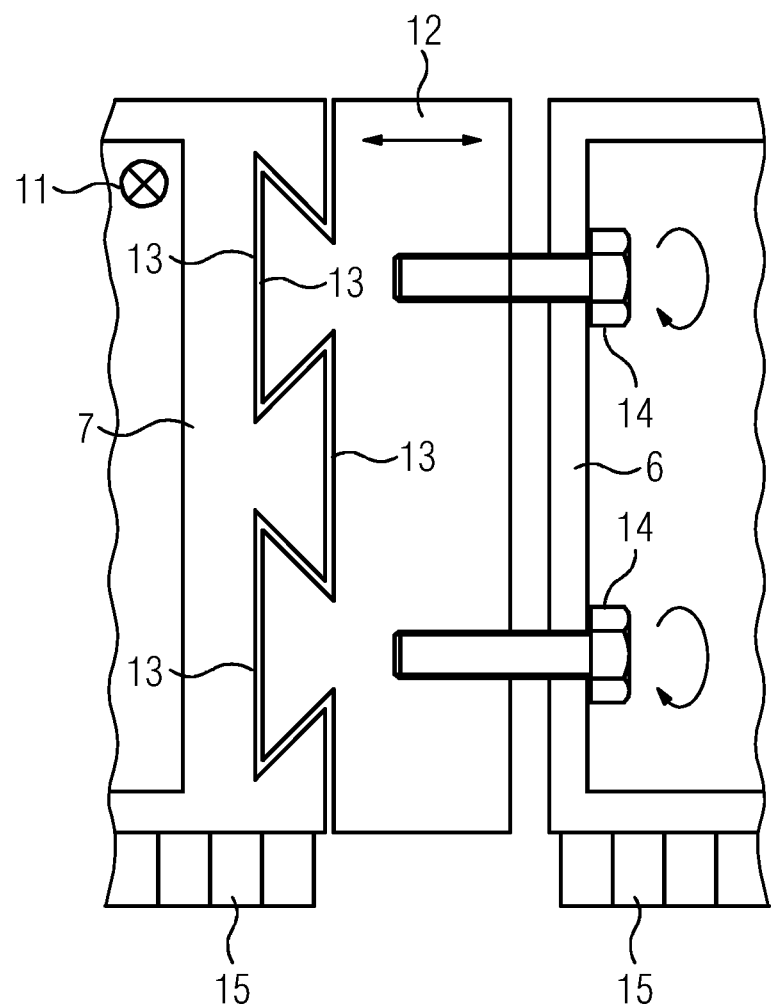
FIG. 2 shows a plan view of a point of connection between a fixed ring sector and a detachable ring sector of a medical imaging system according to an embodiment.

FIG. 2 shows an example of such releasable connections in plan view. A detachable ring sector 7 is shown on the left-hand side, and a fixed ring sector 6 is shown on the right-hand side. Both sectors are connected by a guide element 12 that is shown as part of the fixed ring sector 6. A screw system is used to screw the guide element 12 tightly by screws 14 to the rest of the fixed ring sector 6. The guide element 12 is interlocked mechanically with the detachable ring sector 7 via a guide profile 13 such that the detachable ring sector may be removed only towards the patient aperture, indicated by movement arrow 11. The guide profile 13 may thus, for example, have teeth protruding in the relevant direction (e.g., radial direction with respect to the ring 10) that are shaped so as to impede movement in an axial direction of the ring 10. To remove the detachable ring sector 7, this ring sector slides along the guide element 12 in the desired direction (e.g., towards the patient aperture/center of rotation) using the guide profile 13, and may be removed at the end. The detachable ring sector 7 may then also be re-inserted in a corresponding manner, and for the purpose of readjustment, the guide element 12 may then be clamped by the screw system to provide that the ring is stable. The screw system may be tightened purely manually or using an electric motor.

The ring 10 has an electric drive to provide LAO/RAO angulation for X-ray imaging. This is done by at least two separate drive elements 8 (see FIG. 1) (e.g., motors) that drive the entire ring 10 via ring-gear elements 15. The angular offset of the drive elements is selected according to the joints (e.g., the joints between the detachable ring sectors and the fixed ring sectors) such that movement is provided regardless of an LAO/RAO angulation. This provides, in general, that at least one drive element 8 is always active.

Figure 3:
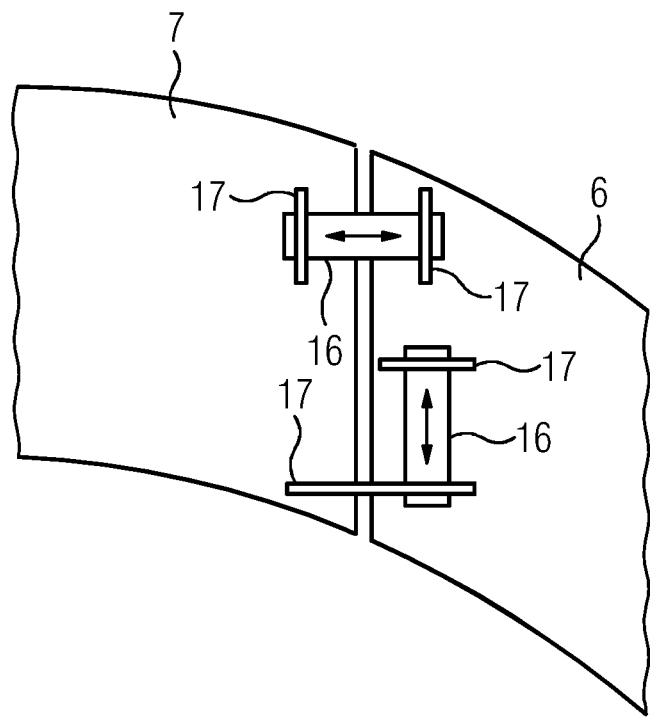
FIG. 3 shows a side view of a point of connection between a fixed ring sector and a detachable ring sector of a medical imaging system according to an embodiment, in which a pin is closed.
Figure 4:
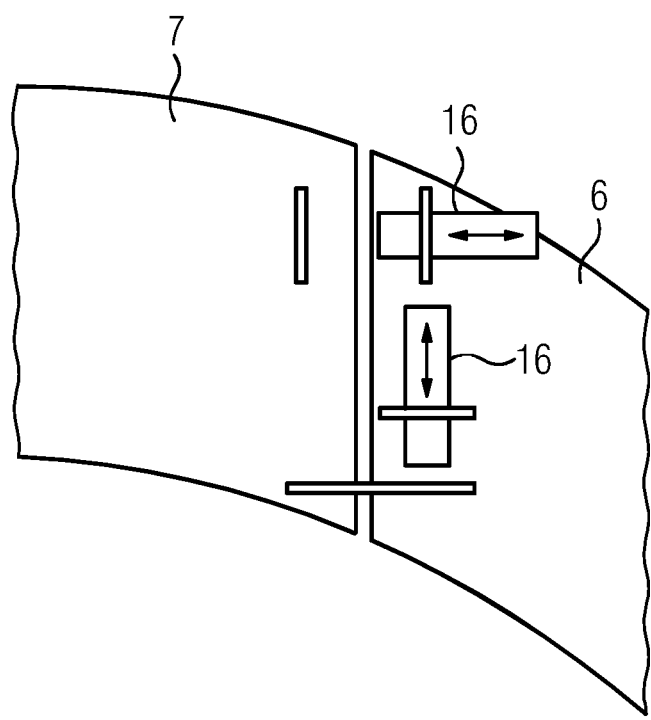
FIG. 4 shows a side view similar to FIG. 3 in which a pin is open.

FIGS. 3 and 4 show, as a further embodiment, a side view of a joint between a detachable ring sector 7 and a fixed ring sector 6. Each of the fixed ring sector 6 and the detachable ring sector 7 is connected to each other by pins 16. For this purpose, the pins 16 travel into corresponding guide sleeves 17 in order to provide mechanical stability with regard to, for example, the detachability of the detachable ring sector 7 and the play produced by manufacturing tolerances. In FIG. 3, the pins 16 have been inserted into the guide sleeves 17 with the result that movement is not possible. In FIG. 4, the pins 16 have been retracted from the guide sleeves 17, with the result that the detachable ring sector 7 may be removed towards the patient aperture or center of rotation by a suitable lifting movement. The pins 16 may be inserted and retracted manually or using an electric motor.

Figure 5:
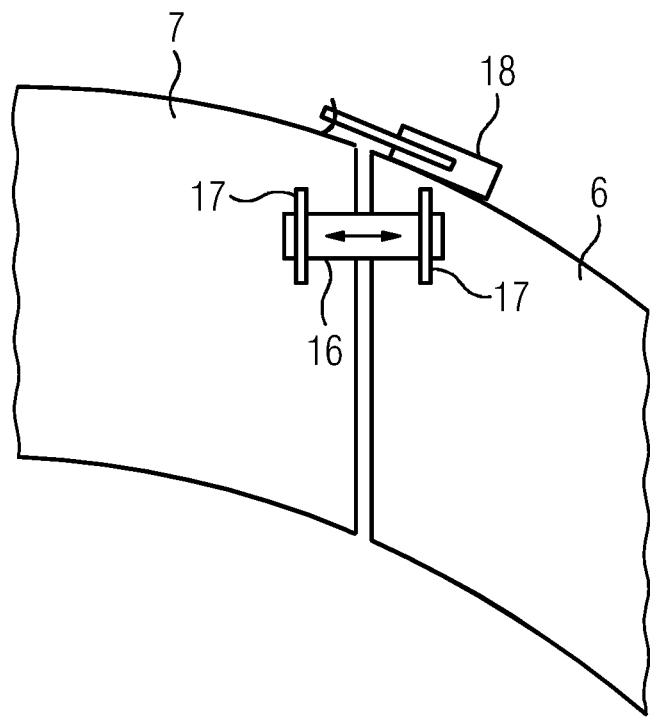
FIG. 5 shows a side view of a point of connection between a fixed ring sector and a detachable ring sector of a medical imaging system according to an embodiment, in which a hinged fastener is closed.
Figure 6:
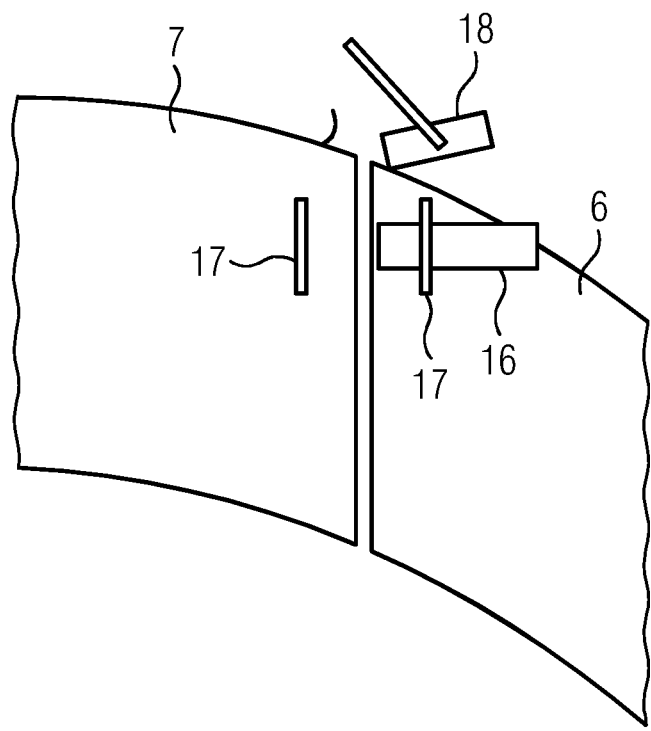
FIG. 6 shows a side view similar to FIG. 5 in which a hinged fastener is open.

Alternatively or additionally, the connection between the detachable ring sector 7 and the fixed ring sector 6 may be secured by one or more hinged fasteners 18, as shown in FIGS. 5 and 6 in a side view. A hinged fastener 18 of this type provides the mechanical stability with regard to the play produced by manufacturing tolerances. In FIG. 5, the pin 16 is closed in the guide sleeve 17, and also, the hinged fastener 18 is closed. In FIG. 6, the pin 16 has been moved outside the guide sleeve 17, and the hinged fastener 18 is open. Once again, the detachable ring sector may thereby perform a lifting movement towards the patient aperture/center of rotation and may be removed. The hinged fastener may be opened manually or using an electric motor.

Figure 7:
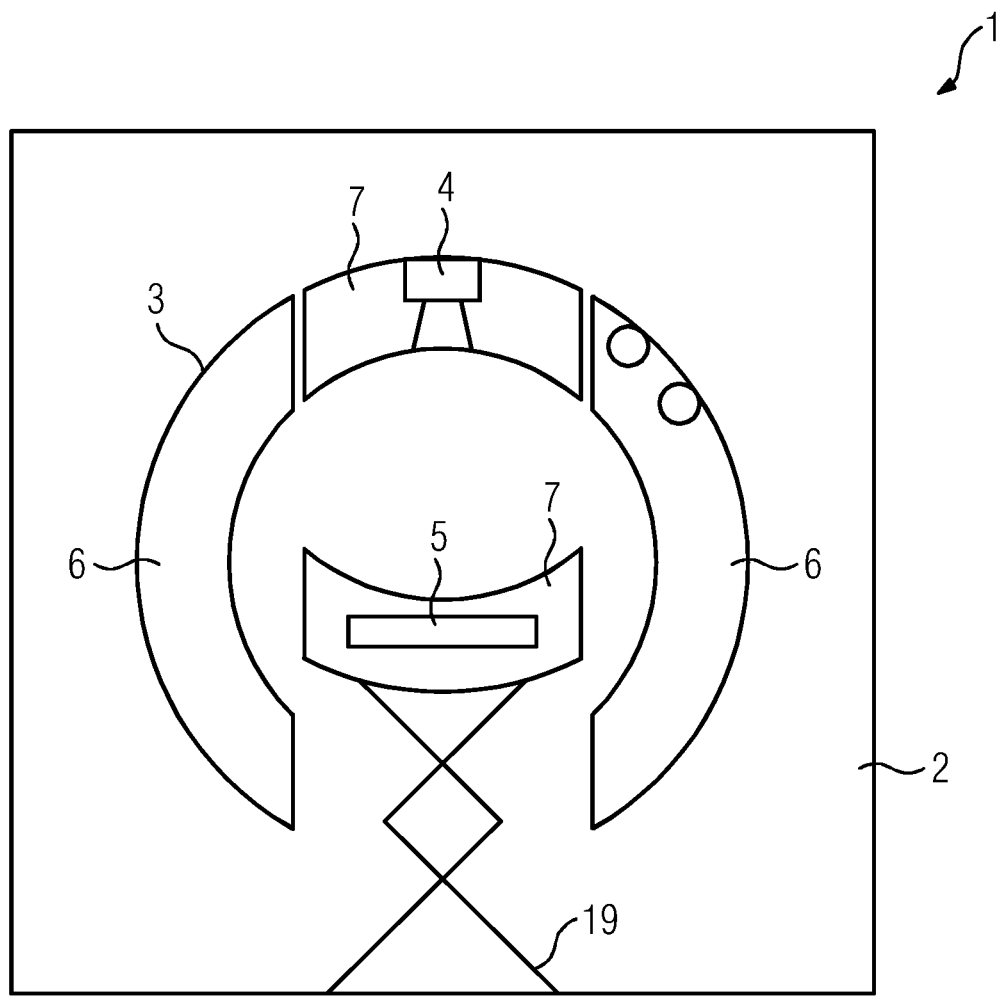
FIG. 7 shows a view of a medical imaging system according to an embodiment having a lifting system.

FIG. 7 shows a lifting system that may be used to remove the detachable ring sector 7 from the ring. The lifting system may be permanently built into the medical imaging system or may be added if required. If all the connecting elements present are open, then a scissor lift 19, which is fitted in the medical imaging system 1, may be coupled to the detachable ring sector 7, and may lift the ring sector out of the ring towards the patient aperture/center of rotation. Then, the detachable ring sector may be removed entirely from the imaging system if required, or assembly, maintenance or replacement is performed while the detachable ring sector is located in the patient aperture. A reverse sequence of operation may include the following acts: the detachable ring sector is inserted into the ring using the lifting system; the connecting elements fix the detachable ring sector in the ring; the mechanical coupling of the lifting system to the detachable ring sector is released (e.g., a pin connection); and the lifting system is removed from the detachable ring sector (e.g., moved into a parked position).

The medical imaging system can also include more than four ring sectors, although at least two detachable ring sectors are again present. The detachable ring sectors carry the X-ray tube and the X-ray detector. If there are two or more X-ray tubes and X-ray detectors present, then more detachable ring sectors may also be present. The lifting system may also be formed by a jackscrew lifting system, for example.

It is possible to provide adequate access to specific technical components of the X-ray imaging unit inside the magnetic resonance imaging unit quickly and with little effort using the medical imaging system according to one or more of the present embodiments. It is hence possible, for example, to replace or repair the X-ray tube and the X-ray detector easily. Once the detachable ring sector has been taken out of the ring towards the patient aperture/center of rotation, the detachable ring sector may be picked up (e.g., by a forklift truck) and taken out of the medical imaging system completely. This allows servicing work and assembly tasks to be performed in the usual manner. This makes all types of maintenance and repair work easier. The present embodiments provide reliable operation of the medical imaging system without limitations and with full accessibility both to the magnetic resonance imaging unit and to the X-ray imaging unit. The combined magnetic resonance and X-ray imaging thus makes a major contribution to comprehensive diagnosis of all forms of diseases and injuries.

The present embodiments may be summarized briefly as follows. For the purpose of particularly reliable and comprehensive patient care, a medical imaging system for combined magnetic resonance and X-ray imaging is provided. The system includes a magnetic resonance imaging unit and an X-ray imaging unit that are connected to each other mechanically such that the X-ray imaging unit is built into the magnetic resonance imaging unit and both units surround a patient aperture. The X-ray imaging unit includes a ring that has an X-ray tube and an X-ray detector and may rotate about the patient aperture. The ring is composed of at least four ring sectors, of which two ring sectors may be detached from the ring, and at least two ring sectors are fixed in place. An X-ray detector is arranged on one of the detachable ring sectors, and an X-ray source is arranged on the other of the detachable ring sectors.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical imaging system for combined magnetic resonance and X-ray imaging, the medical imaging system comprising:
    a magnetic resonance imaging unit; and
    an X-ray imaging unit,
    wherein the magnetic resonance imaging unit and the X-ray imaging unit are connected to each other mechanically such that the X-ray imaging unit is built into the magnetic resonance imaging unit and the magnetic resonance imaging unit and the X-ray imaging unit surround a patient aperture,
    wherein the X-ray imaging unit comprises a ring that has an X-ray tube and an X-ray detector, the ring being rotatable about the patient aperture,
    wherein the ring is composed of at least four ring sectors, two ring sectors of the at least four ring sectors being detachable from the ring and at least two ring sectors of the at least four ring sectors being fixed in place, and
    wherein the X-ray detector is arranged on one of the two detachable ring sectors, and the X-ray tube is arranged on the other of the two detachable ring sectors.

2. The medical imaging system of claim 1, wherein the magnetic resonance imaging unit comprises a solenoid that surrounds the X-ray imaging unit.

3. The medical imaging system of claim 1, wherein the two detachable ring sectors are formed such that the two ring sectors are detachable from the ring towards the patient aperture.

4. The medical imaging system of claim 1, wherein the two detachable ring sectors are connected to the at least two fixed ring sectors by releasable connecting elements.

5. The medical imaging system of claim 1, wherein at points of connection to the at least two fixed ring sectors, the two detachable ring sectors comprise guide elements having complementary guide profiles.

6. The medical imaging system of claim 1, wherein the ring comprises an electric drive having at least two drive elements and a plurality of ring-gear elements that engage with one another and cause the ring to rotate.

7. The medical imaging system of claim 1, wherein the medical imaging system comprises a lifting system for automatic removal of the two detachable ring sectors from the medical imaging system.

8. The medical imaging system of claim 7, wherein the lifting system is dockable onto the two detachable ring sectors.

9. The medical imaging system of claim 4, wherein the releasable connecting elements comprise screws, pins, guide sleeves, hinged fasteners, or any combination thereof.

10. The medical imaging system of claim 2, wherein the two detachable ring sectors are formed such that the two ring sectors are detachable from the ring towards the patient aperture.

11. The medical imaging system of claim 2, wherein the two detachable ring sectors are connected to the at least two fixed ring sectors by releasable connecting elements.

12. The medical imaging system of claim 11, wherein at points of connection to the at least two fixed ring sectors, the two detachable ring sectors comprise guide elements having complementary guide profiles.

13. The medical imaging system of claim 12, wherein the ring comprises an electric drive having at least two drive elements and a plurality of ring-gear elements that engage with one another and cause the ring to rotate.

14. The medical imaging system of claim 13, wherein the medical imaging system comprises a lifting system for automatic removal of the two detachable ring sectors from the medical imaging system.

15. The medical imaging system of claim 14, wherein the lifting system is dockable onto the two detachable ring sectors.

* * * * *